United States Patent [19]

Brody

[11] Patent Number: 4,611,341
[45] Date of Patent: * Sep. 9, 1986

[54] MULTIPLE-ENERGY X-RAY SUBSTRACTION IMAGING SYSTEM

[75] Inventor: William R. Brody, Palo Alto, Calif.

[73] Assignee: The Board of Trustees of the Leland Stanford Junior University, Stanford, Calif.

[*] Notice: The portion of the term of this patent subsequent to Apr. 24, 2001 has been disclaimed.

[21] Appl. No.: 577,074

[22] Filed: Feb. 6, 1984

Related U.S. Application Data

[63] Continuation of Ser. No. 260,694, May 5, 1981, Pat. No. 4,445,226.

[51] Int. Cl.$^4$ ............................................. G03B 41/16
[52] U.S. Cl. ........................................ 378/99; 358/111
[58] Field of Search ....................... 378/99, 5; 358/111

[56] References Cited

U.S. PATENT DOCUMENTS 3,974,386  8/1976  Mistretta ............................... 378/99
4,029,963  6/1977  Alvarez ................................... 378/5

Primary Examiner—Craig E. Church
Attorney, Agent, or Firm—Flehr, Hohbach, Test, Albritton & Herbert

[57] ABSTRACT

Projection measurements are made at different parts of the x-ray energy spectrum. These measurements are processed to obtain image data with the soft tissue component eliminated. The processed image data is obtained before and after the administration of a contrast agent. The two sets of processed image data are combined to obtain an isolated image of the contrast agent which is immune to motion of soft tissue. The invention described herein was made in the course of work under a grant from the Department of Health, Education, and Welfare.

3 Claims, 2 Drawing Figures

MULTIPLE-ENERGY X-RAY SUBSTRACTION IMAGING SYSTEM

This is a continuation, of application Ser. No. 260,694 filed on May 5, 1981, now U.S. Pat. No. 4,445,226.

BACKGROUND

1. Field of the Invention

This invention relates to x-ray imaging systems. In a primary application the invention relates to obtaining isolated images of an administered contrast agent.

2. Description of Prior Art

There has recently been a great interest in obtaining images of blood vessels using a noninvasive administration of an iodinated contrast agent. This avoids the dangerous, painful and expensive procedure of inserting catheters into arteries using a surgical procedure. The most common present method of accomplishing this is known as digital radiography. In this approach fluoroscopic television images are taken both before and after the administration of a contrast agent, digitally stored, and subtracted to provide an image of the iodine only. The problem with this system is clearly motion. Any motion between the two stored images will result in severe artifacts in the subtracted image and distort or obliterate the desired image of the iodinated vessel. Even if the patient holds still, he is subject to many involuntary motions of soft tissue structures such as swallowing, respiratory motion, cardiac motions and peristalsis. A description of the system is given in the paper by T. Ovitt, et al., "Development of a Digital Video Subtraction System for Intravenous Angiography," Proceedings of the SPIE Conference on Recent and Future Developments in Medical Imaging II, Vol. 205, August 1979, pp. 73-76.

The motion problem can be eliminated by the system described in U.S. Pat. No. 3,848,130 issued to A. Macovski. In this patent, images of various materials are made by making measurements at different regions of the x-ray energy spectrum. These measurements are processed to obtain the desired material images. In this way, iodine can be imaged after administration, without requiring temporal subtraction. In many cases, however, it is difficult or inconvenient to make all of the desired spectral measurements. For example, the separation of iodine from both bone and soft tissue could require measurement at three different energy spectra. The required energy switching can be difficult to accomplish. Also, it is often difficult to efficiently generate all of the desired energy spectra. For example, if a very low energy spectrum is required, below the iodine k edge, the x-ray tube exhibits very low efficiency. It has been found convenient, therefore, to use this selective material imaging system with fewer spectral measurements. If two spectral measurements are made, a more limited set of materials can be separated. For example, two measurements at the lower and upper regions of the diagnostic x-ray spectrum can be processed as described in 3,843,130, to provide an image of iodine and bone components, with the soft tissue cancelled. Similarly, these same two measurements can be combined to obtain an image of iodine and soft tissue, with the bone cancelled. A system of this type is described in a paper by R. E. Alvarez, et al., "Energy Information in X-ray Imaging," Proceedings of the SPSE Conference on Image Analysis Techniques and Applications, January 1981, pp. 150-154. This system, using two spectral measurements, does not, however, provide an isolated image of iodinated blood vessels, free of intervening tissue.

A preferred processing system is described in U.S. Pat. No. 4,029,963, issued to R. E. Alvarez and A. Macovski. Here the two spectral measurements are subjected to a nonlinear processing system to provide two energy-independent components; the Compton scattering component and the photoelectric component. These represent primarily the density and atomic number of each material respectively. Using these two processed data sets, any material can be cancelled by using a linear weighted sum of the two components. This process is described in the previously referenced paper by R. E. Alvarez.

SUMMARY OF THE INVENTION

An object of the invention is to provide a method and apparatus for obtaining isolated images of an administered contrast material. A further object of the invention is to eliminate the motion artifacts obtained in temporally subtracted images of iodinated contrast agents. A further object of the invention is to eliminate the undesired tissue components obtained in dual-energy images of iodinated contrast agents.

Briefly, in accordance with the invention, projection measurements are made at different x-ray energy spectra. These measurements are processed to obtain image data where the soft tissue components have been cancelled. Image data of this type is obtained both before and after the administration of the contrast agent. The two sets of image data are subtracted to provide an isolated contrast image immune to soft tissue motions.

BRIEF DESCRIPTION OF THE DRAWINGS

For a more complete disclosure of the invention, reference may be made to the following detailed description of several illustrative embodiments thereof which is given in conjunction with the accompanying drawings, of which.

DESCRIPTION OF THE PREFERRED EMBODIMENT

Figure 1:
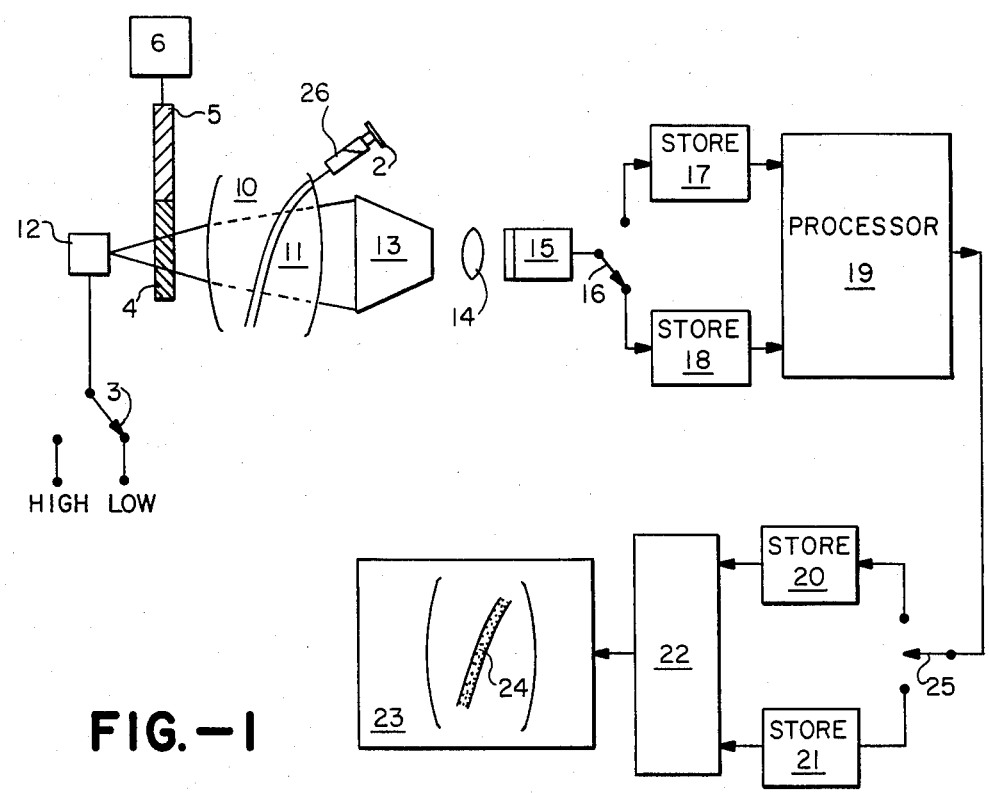
FIG. 1 is a block diagram of an embodiment of the invention using a sequential variation in the energy of the source.

An understanding of the broad aspects of the invention may best be had by reference to FIG. 1 of the drawings. It is desired to make an image of blood vessel 11 in a region of the body 10. In the prior art, images were taken before and after the intravenous administration of an iodinated contrast agent 26 using syringe 2 and subtracted. These images are often distorted by motion artifacts due to involuntary soft tissue motions occurring between the two images.

In this invention, prior to administering contrast agent 26, x-ray source 12 is used to provide images at two parts of the x-ray energy spectra. This is accomplished by sequentially altering the source energy. Switch 13 is used to switch the anode voltage on x-ray source 12 between a high and low voltage. These voltages can be approximately 130 $KV_p$ and 80 $KV_1$ respectively. alternatively the source energy can be varied by inserting x-ray filtration. Activator 6 can be used to insert filter 4 or filter 15 in front of the x-ray source. Filter 4 can provide a lower energy spectrum using, for example, a gadolinium filter material having a K edge while filter 5 can provide a higher energy source by using, for example, a copper filter material providing beam hardening. For optimum spectra both the voltage switching and the filter changing are used to provide a low energy spectrum of about 40–70 kev and a high energy spectrum of about 70–120.

Each source spectrum is sequentially projected through a region of the body 10 onto image intensifier 13. The resultant light image is imaged, using lens 14 onto television camera 15. The projection measurements corresponding to each energy spectra are than stored on storage systems 17 and 18 with, for example, the higher energy image stored on store 17 and the lower energy image stored on store 18. These are generally digital storage systems. Therefore the output in the TV camera must be applied to an analog-to-digital converter, not shown, and then applied to switch 16. This switch applies the digital signal to store 17 when the high energy source is used and to store 18 when the low energy source is used.

In accordance with the previously referenced U.S. Pat. No. 3,848,130 the stored measurements at each energy spectra can be processed to provide selective material imaging. Using the two measurements, a limited class of materials can be selected. Here the processor 19 provides substantial cancellation of the soft tissue components so that the processed data set contains information primarily of bone. Cancellation of soft tissue is provided since it represents the source of involuntary motions such as swallowing, breathing, heartbeat, pulsating vessels, peristalsis, etc. If a patient is asked to hold still during an intravenous injection he can usually reliably hold his bone structure steady. Therefore the bone motion is not a problem.

This first processed data set from processor 19 is sorted, for example, in digital store 20 using switch 25. Following intravenous administration of contrast agent 26, usually an iodinated material, using syringe 2 an appropriate time is allowed to pass until the iodine reaches the vessel to be imaged 11. This can represent, for example, the the aorta or the carotid artery. The entire dual energy imaging process is then repeated using the two source energies, this time in the presence of the iodinated contrast agent. Processor 19 again takes the two measurement sets and produces a processed data set where the soft tissue has been substantially cancelled so that soft tissue motion cannot cause artifacts. The second data set contains both bone and the iodine image information. This second data set is stored in digital store 21 using switch 25.

Storage systems 20 and 21 essentially contain bone images without and with the iodinated contrast image information. Combiner 22 can simply be a subtraction operation which subtracts the data set in 20 from the data set in 21 to provide an isolated image of the iodinated contrast agent in the vessel 24 in display monitor 23. Since the bone image is the same in both data sets, the difference is the iodine alone. The resultant image is immune to soft tissue motions since energy information is used to cancel the soft tissue prior to the final subtraction.

A preferred system for processor 19 is that described in the previously referenced U.S. Pat. No. 4,029,963 and in the previously referenced paper by R. E. Alvarez. Here, using nonlinear functions, the measurement data at the two energy spectra are processed to provide two energy-independent data sets. These can represent the Compton scattering and photoelectric components or, alternatively, two specific material components such as calibration materials aluminum and plastic. A linear weighted sum of these two energy-independent components can be used, for example, to cancel any material. For this system the appropriate weights are used to cancel the soft tissue.

As to the nonlinear functions used in processor 19; in the referenced material the logs of the measurements are derived. These logs are then applied to a polynomial nonlinear equation to extract the line integrals of the two desired basis components. If, for example, monoenergetic x-rays at different energies were used, only the logarithm plus linear processing would be necessary to provide the desired line integrals. The nonlinear polynomials correct for the nonlinearities caused by beam hardening.

Figure 2:
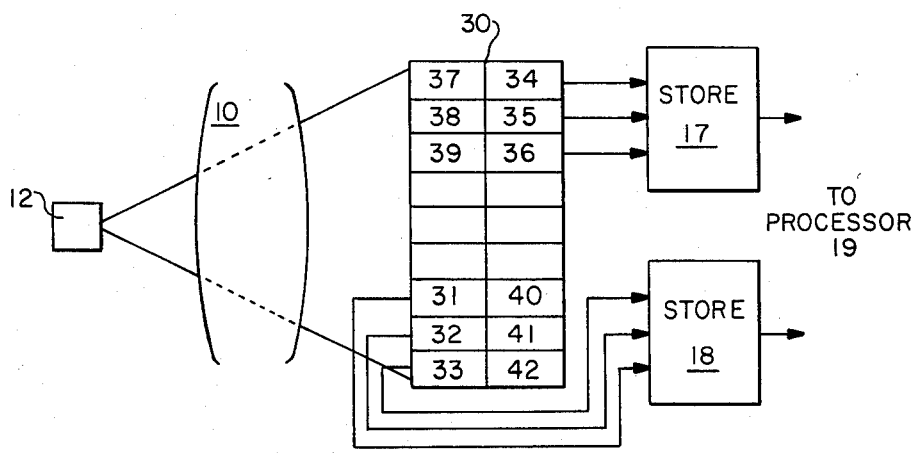
FIG. 2 is a block diagram of an embodiment of the invention using an energy-selective detection system.

In the system of FIG. 1 the energy measurements are taken in sequence. Although these can be taken rapidly, there is the possibility of motion between the two measurements. In FIG. 2 these measurements are taken simultaneously using the energy-sensitive detector 30. Source 12 is the conventional broad-energy x-ray source encompassing the diagnostic energy spectrum. The transmitted radiation is projected through the body 10 to detector array 30.

Each element of the array consists of a front and back part. As described in U.S. Pat. No. 4,029,963, the lower energy x-rays interact primarily in the front part of the detector while the higher energy x-rays interact primarily in the back part of the detector. The detector material can be a scintillator such as sodium iodide, in which case photodetectors are used to measure the light output at the front and back parts. Alternatively the detector material can be a highpressure gas, such as Xenon, in which case isolated wires are used to individually collect the charge in the front and back parts. For clarity, three wires are shown collecting low-energy measurement signals from the front halves and high-energy measurement signals from the back halves. Front detector elements 31, 32 and 33 have their low-energy measurements stored in digital store 18, as with the system in FIG. 1. Similarly, back detector elements 34, 35 and 36 have their high-energy measurements stored in digital store 17. Although the connections are not shown, for clarity, front detectors 37, 38 and 39 are connected to store 18 and back detectors 40, 41 and 42 are connected to store 17. These measurements are processed in processor 19 exactly as in the system in FIG. 1, with the remainder of the system being identical and thus not shown. In FIG. 2, however, the high and low energy measurement signals are derived simultaneously using energy selective detectors. As before, these measurements are made both before and after the administration of the contrast agent.

Array 30 could be a two-dimensional array encompassing the entire image. For economic reasons, however, it is preferable to use a single line array. This line array is scanned along the image plane, with respect to the body 10, to provide a complete image measurement set. Alternatively the detector can be stationary and the patient 10 scanned as is done in the commercially available GE Scoutview system.

If a one line scanned array is used, it is useful to provide a beam collimator between the source 12 and the patient 10 to limit the radiation to the line being detected. This not only reduces the dose, but also minimizes the received scattered radiation. It should be pointed out, however, that this system has an inherent immunity to the effects of scatter. Since data taken before and after contrast administration is subtracted, most of the scatter components will be cancelled. Therefore the system of FIG. 1, which does not have single line collimator but images the entire volume simultaneously, will also have a high immunity to the effects of scatter.

The embodiments described showed two energy measurements before and after the administration of a contrast agent. The invention is clearly much broader in concept. It may often be desirable to cancel a variety of materials which may exhibit motion during the period before and after contrast administration. Thus a plurality of energy measurements, as described in U.S. Pat. No. 3,848,130, would be used to provide the required selectivity before and after the administering of the contrast agent. Although iodinated contrast agents were used as an example for vessel imaging, many others can be used including barium, xenon, tantalum, etc.

What is claimed is:

1. Apparatus for providing an isolated image of an iodinated contrast material administered into a region of the body comprising:

means for making separate x-ray transmission measurements at the lower and upper parts of the diagnostic x-ray spectrum, said lower part being in the spectrum of 40–70 Kev and said upper part being in the spectrum of 70–120 Kev;

means for processing these measurements to produce a data set representing projection image data where the soft tissue information has been substantially cancelled; and means for subtracting data sets representing measurements taken before and after the administration of the iodinated contrast material to provide image information representing substantially only the iodine content whereby soft tissue motions have been cancelled.

2. Apparatus as described in claim 1 wherein the means for processing the array of x-ray transmission measurements includes computational means for combining nonlinear functions of the measurements.

3. Apparatus as described in claim 2 wherein the means for processing the two x-ray transmission measurements includes means for first computing two energy-independent sets of data and then combining these sets of data to produce a data set where soft tissue is substantially eliminated.

* * * * *

UNITED STATES PATENT AND TRADEMARK OFFICE
CERTIFICATE OF CORRECTION

PATENT NO. : 4,611,341

DATED : September 9, 1986

INVENTOR(S) : WILLIAM R. BRODY

It is certified that error appears in the above-identified patent and that said Letters Patent is hereby corrected as shown below:

On page 1, after the title, insert the following paragraph on line 4:

--This invention was made with Government support under contract No. HV02922 awarded by the National Institutes of Health. The Government has certain rights in this invention.--

Signed and Sealed this

Thirteenth Day of December, 1994

*Attest:*

BRUCE LEHMAN

*Attesting Officer*  *Commissioner of Patents and Trademarks*